United States Patent
Heine et al.

(10) Patent No.: US 7,871,174 B2
(45) Date of Patent: Jan. 18, 2011

(54) HEADBAND FOR DIAGNOSTIC INSTRUMENTS COMPRISING LIGHT SOURCE AND ACCUMULATOR MODULE

(75) Inventors: Oliver Heine, Herrsching (DE); Dirk Schade, Penzberg (DE); Stefan Knesewitsch, Herrsching (DE); Gerhard Guegel, Diessen (DE); Anton Schneider, Gilching (DE); Elisabeth Gingelmeier, Utting (DE)

(73) Assignee: Heine Optotechnik GmbH & Co. KG, Herrsching (DE)

( * ) Notice: Subject to any disclaimer, the term of this patent is extended or adjusted under 35 U.S.C. 154(b) by 0 days.

(21) Appl. No.: 12/265,067

(22) Filed: Nov. 5, 2008

(65) Prior Publication Data
US 2009/0154143 A1 Jun. 18, 2009

(30) Foreign Application Priority Data
Nov. 7, 2007 (DE) .................. 10 2007 053 095

(51) Int. Cl.
*F21V 21/84* (2006.01)
(52) U.S. Cl. ...................... 362/105; 362/106
(58) Field of Classification Search ................ 362/103, 362/105, 106, 184, 188, 190, 249.01, 249.1
See application file for complete search history.

(56) References Cited

U.S. PATENT DOCUMENTS

| 4,593,683 | A | | 6/1986 | Blaha |
| 4,794,496 | A | * | 12/1988 | Lanes et al. ................. 362/105 |
| 5,774,271 | A | * | 6/1998 | Lagerway et al. ........... 359/649 |
| 7,210,810 | B1 | | 5/2007 | Iversen et al. |
| 2004/0130888 | A1 | * | 7/2004 | Twardawski ................ 362/105 |
| 2005/0047117 | A1 | * | 3/2005 | Scholl et al. ................ 362/106 |
| 2005/0128735 | A1 | | 6/2005 | Atkins et al. |
| 2005/0276036 | A1 | * | 12/2005 | Miles et al. ................. 362/105 |

FOREIGN PATENT DOCUMENTS

DE 2315390 A 10/1973

* cited by examiner

*Primary Examiner*—Hargobind S Sawhney
(74) *Attorney, Agent, or Firm*—Rothwell, Figg, Ernst & Manbeck, P.C.

(57) ABSTRACT

A head band for diagnostic instruments comprising a light source and a battery has, at its back support part (12), a flat housing (21) for adjusting and fixing the head band length by means of a rotary knob (22). An accumulator module (31) optimized with regard to volume, weight and weight distribution can be mounted and detached by means of bayonet-type grooves (25) at the housing (21) and pins (33) at the accumulator module (31), and can be fixed by means of a resilient spring (26) at the housing (21) and a recess (34) in the accumulator module (31) without impairing the function of the rotary knob (22).

7 Claims, 5 Drawing Sheets

Fig. 2
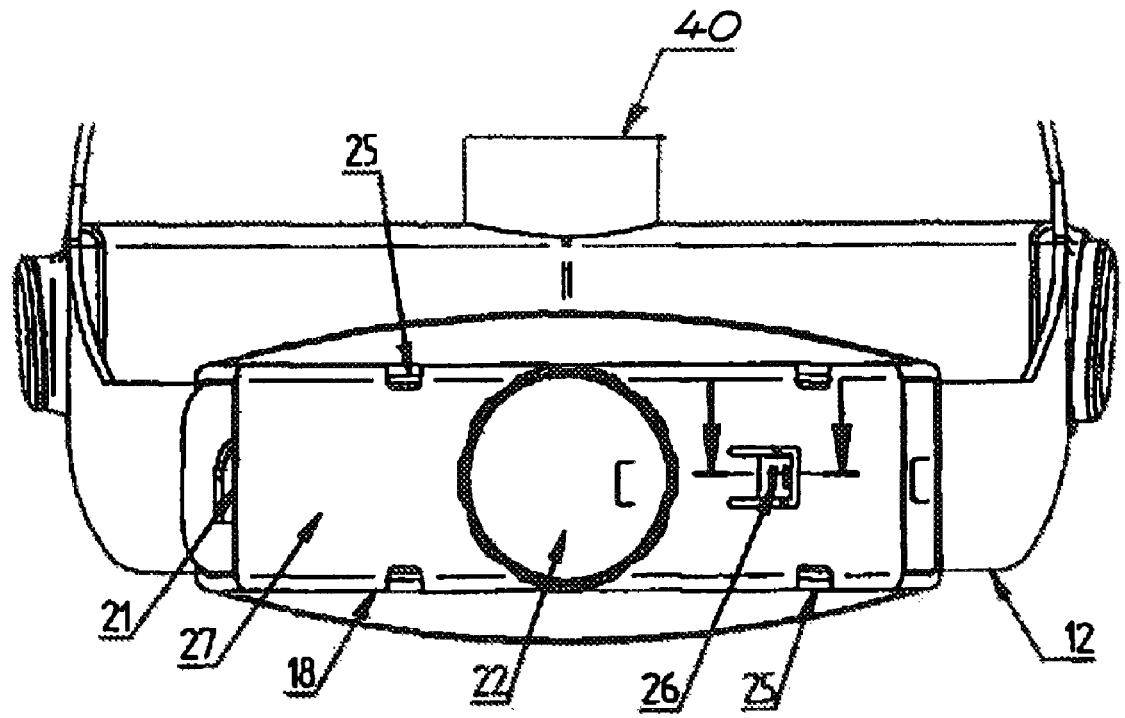
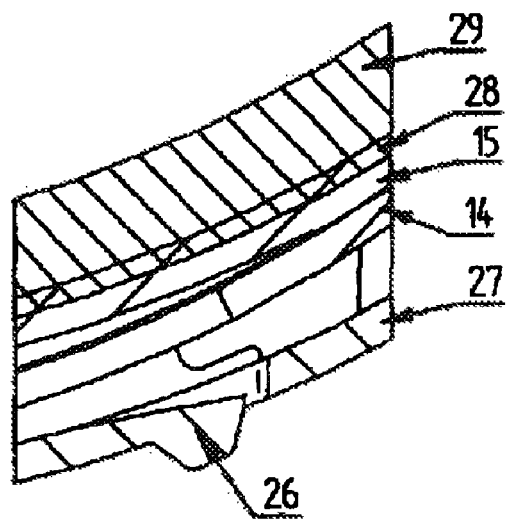
Fig. 3

HEADBAND FOR DIAGNOSTIC INSTRUMENTS COMPRISING LIGHT SOURCE AND ACCUMULATOR MODULE

CROSS-REFERENCE TO RELATED APPLICATION(S)

This application claims the benefit of German Patent Application No. 102007053095.3, filed Nov. 7, 2007, the disclosure of which is incorporated herein in its entirety by reference.

BACKGROUND OF THE INVENTION

1. Field of the Invention

The invention relates to a headband for diagnostic instruments comprising a light source and an accumulator module.

2. Description of the Background Art

For diagnostic instruments carried on the head use is made of batteries or accumulators, hereinafter also referred to as accumulator modules, which are placed directly on the headband. They serve as an energy source for operating a light source carried on the headband.

Such a head band is, for example, known from U.S. Pat. No. 4,593,683. The accumulators are mounted at the back part of the head band in order to contribute to a weight counterbalance with the diagnostic instrument mounted at the forehead side of the person wearing the head band. The head band has, at its back part, two ends overlapping each other which can be fixed with respect to each other for adaptation to the size of the head and in the adjusted position. For this, the ends of the head band, which are guided in an overlapping manner in a housing, are recessed in the longitudinal direction and provided with internal teeth which are engaged by a pinion placed on a shank which extends out of the housing and can be turned by means of a rotary knob.

On the internet at http:\\www.keeler.co.uk the company of Keeler Ltd., GB, presents a head band comprising an opthalmoscope which, at its back part, includes a housing substantially adapted to the form of the head, in which housing the longitudinal adjustment mechanism for the ends of the band and electrical components are arranged and which thus has a large width or thickness. A nose extending above the height of the housing protrudes outwardly from the center of the housing, through which nose the shank extends such that it can be turned, wherein the rotary knob for the head band adjustment is placed at the free end of the shank. The accumulator arrangement consists of two portions connected by an upper bar. The accumulator arrangement can be slipped onto the nose of the housing, wherein contact elements of the accumulator come into contact with contact elements of the housing, thereby providing electric current to be fed into a lamp of the opthalmoscope.

A similar head band is also disclosed in US 2005/0128735 A1. This head band has a battery base unit wherein ends of the head band pass through said battery base unit. An accumulator module can be fitted to said battery base unit wherein two inclined ramps engage in two inclined recesses and a clip locks in place.

U.S. Pat. No. 7,210,810 B1 describes a head band comprising a closed front support part for a diagnostic instrument having an LED and comprising an open back support part, wherein a mechanism for adjusting and fixing the head band length is assigned to the ends of said open back support part, the mechanism having clasps substantially adapted to the shape of the human head and a rotary knob. Said mechanism is provided with a receiving means in which a battery clip can be inserted.

The prior art accumulator systems are not optimized with regard to volume and weight. The special complex assembly means for the accumulator render the back part of the head band very heavy. Moreover, the shape of these assembly means is not adapted ideally to existing head band geometries.

SUMMARY OF THE INVENTION

The object of the invention therefore is to provide a head band having an accumulator module optimized with regard to weight and volume which can be easily mounted and detached without thereby impairing the head band adjustment through a rotary knob.

This object is achieved by a head band comprising a closed front support part for a diagnostic instrument having a light source, an open back support part having two opposite ends, a mechanism for adjusting and fixing the length of said head band and associated to said ends of said open back support part, said mechanism being arranged in a housing substantially adapted to a shape of a human head and having a shank extending through a wall of said housing and comprising a rotary knob, and an accumulator module which can be detachably mounted at said housing and has an opening for a passage of said shank and said rotary knob and to which a cable connection to said light source is associated. Said housing is a flat housing having two opposing rims, wherein two spaced-apart bayonet-type grooves are formed in each of said opposing rims of said flat housing and wherein said flat housing has a resilient spring protruding from an outer wall thereof. Said opening in said accumulator module is a central, fully bordered opening having a shape which is adapted to the geometry of said rotary knob for operation thereof. Said accumulator module has pins arranged for engagement within said grooves in said flat housing and for lateral shifting within said grooves such that said pins occupy a fixed position in said grooves. Said accumulator module has a recess for snap engagement with said resilient spring of said flat housing in a fixed position of said pins in said grooves.

The head band according to the invention has the advantage that an accumulator module optimized with regard to weight, weight distribution and volume can without any problems be installed at and removed from the head band without impairing the rotational operation of the rotary knob for the head band length adjustment.

In a preferred embodiment of the head band of the present invention said pins are arranged at equal lateral distances to said opening.

Preferably the thicknesses of each of said outer wall and an inner wall of said flat housing substantially correspond to a thickness of said head band.

In another preferred embodiment of the head band of the present invention said accumulator module comprises narrow end sides, in the area of each of said narrow end sides a three-pole plug socket for a cable connection being provided.

Preferably said accumulator module, on a side thereof facing away from said flat housing, is tapered towards said opening.

BRIEF DESCRIPTION OF THE DRAWINGS

The invention is explained in greater detail by way of example with reference to drawings, wherein

FIG. 2 is a plan view of a part of the head band of FIG. 1, seen from behind;

FIG. 3 is a cross section along the line C-C of FIG. 2;

DETAILED DESCRIPTION OF THE INVENTION

Figure 1:
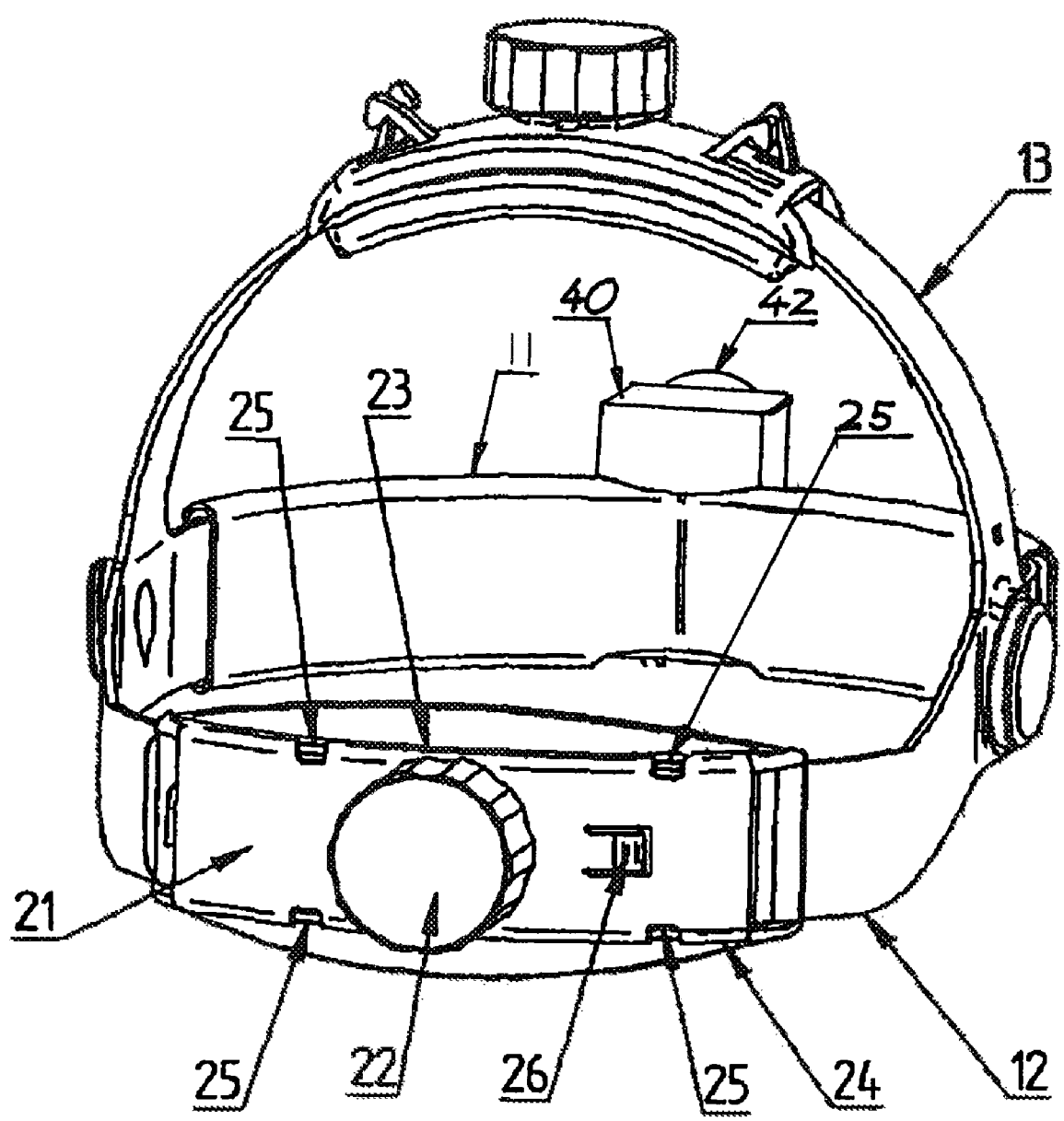
FIG. 1 shows an embodiment of the head band according to the invention, seen from behind, without accumulator module.

The head band shown in FIG. 1 has a front support part 11 and a back support part 12 as well as an upper support part 13 connected with them. The front support part 11 is located at the forehead side of the head of the person wearing the head band and serves to mount and hold a diagnostic instrument 40, such as an opthalmoscope, in which a light source 42 is integrated.

A flat housing 21 is placed at the back support part 12. It can be seen from FIG. 3 that the flat housing 21 has a thin outer wall 27 and a thin inner wall 28, between which the ends 14 and 15 of the head band are arranged in an overlapping manner and can be adjusted by a known adjustment mechanism, not shown, with respect to one another such that by turning the rotary knob 22 in one direction the head band is enlarged and in the other direction the head band is narrowed. The thicknesses of the outer wall 27 and the inner wall 28 substantially correspond to that of the head band and are dimensioned such that the flat housing 21 is sufficiently rigid and stable for holding an accumulator module 31 shown in FIG. 4. A lining 29 is applied to the inner wall 28, which lining 29 comes to abut on the back of the head of the person wearing the head band.

Two spaced-apart bayonet-type grooves 25 for mounting the accumulator module 31 are recessed in each of the upper rim 23 and the lower rim 24 of the flat housing 21. A resilient spring 26 protrudes from the outer wall 27 of the flat housing 21 at the right side of the rotary knob 22 in FIG. 1. As can be seen from FIG. 3, the spring 26 is formed by a projection placed on a spring arm, which projection is biased in the direction away from the outer wall 27.

Figure 4:
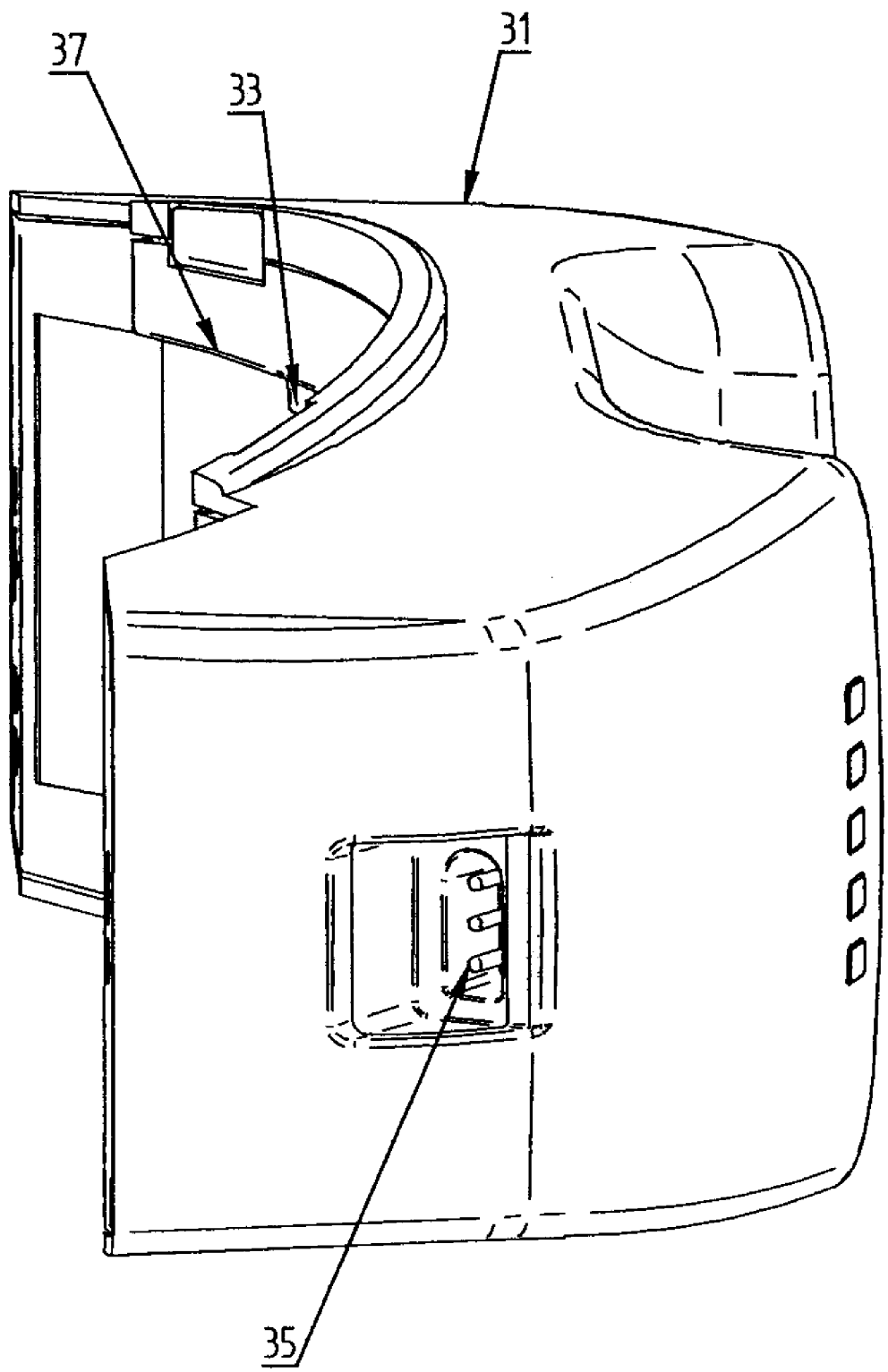
FIG. 4 is a perspective side view of the accumulator module.
Figure 8:
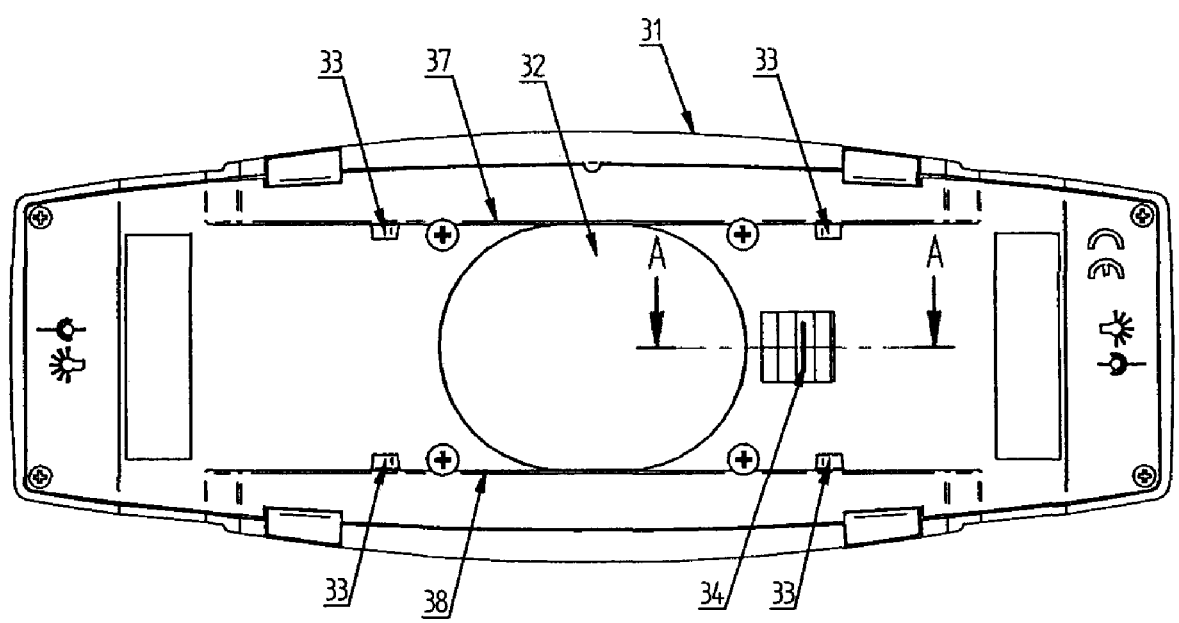
FIG. 8 shows the accumulator module, seen towards its left side in FIG. 4.

The accumulator module 31 shown in FIGS. 4 and 8 has a three-pole plug socket 35 at each of its opposing ends for connecting to a corresponding plug of a connection cable, not shown, of a charging device or the light source 42.

Figure 5:
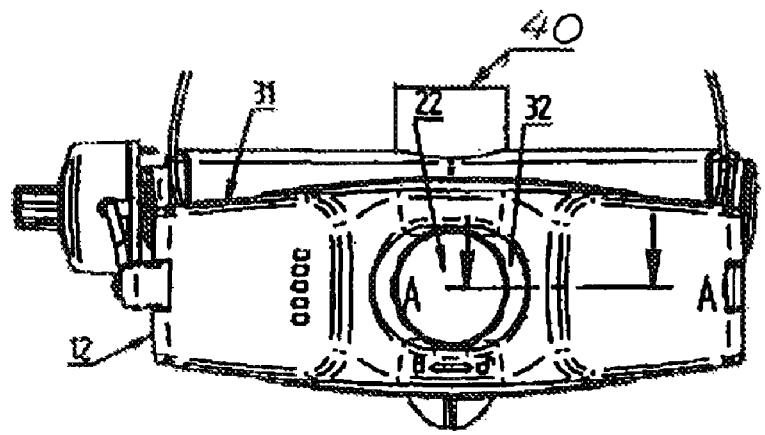
FIG. 5 is a view of the head band as in FIG. 2, with the accumulator module attached.
Figure 6:
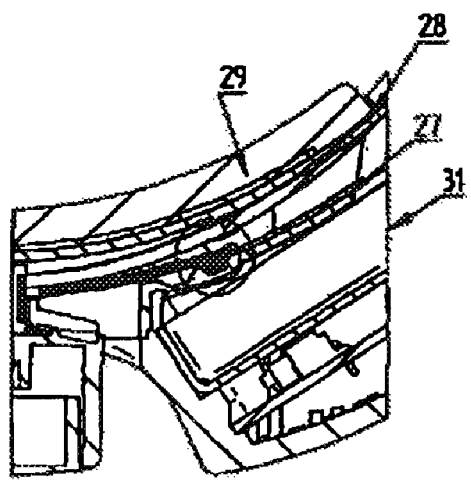
FIG. 6 is a cross section along the line A-A of FIG. 5.
Figure 7:
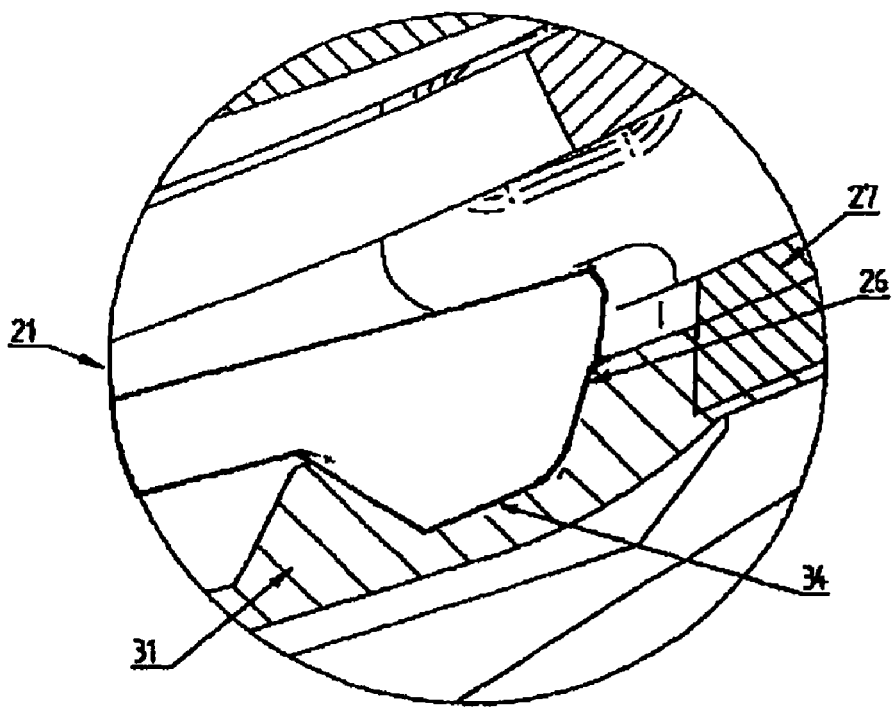
FIG. 7 is an enlarged view of the detail marked by the circle in FIG. 6.

FIGS. 5 to 7 show the head band with a slipped-on accumulator module 31. The opening 32 of the accumulator module 31 is oval and designed such that, in the final fixing position of the accumulator module 31, the rotary knob 22 is located at the center of the opening 32 and thus can be easily gripped. Since the rotary knob 22 does not protrude beyond the outer surfaces of the accumulator module 31, but is in fact arranged more towards the inside in the direction of the head band due to the construction of the accumulator module 31, which is retracted in the area of the opening 32 (see also FIG. 4 at the top right side), the volume of the accumulator module 31 can be optimally designed, wherein the weight is distributed symmetrically to the opening 32 towards the left and the right side.

FIG. 8 shows the inward side of the accumulator module 31. Pins 33 which serve to connect the accumulator module 31 to the flat housing 21 are provided symmetrically to the oval opening 32, at the top and the bottom on the left and the right sides of the oval opening 32, at a longitudinal edge 27, 38. The connection is effected in such a manner that the accumulator module 31 is moved with the surface shown in FIG. 8 towards the outer wall 27 of the housing 21 such that the pins 33 are inserted into the grooves 25. As can be seen from FIG. 2, the grooves 25 are offset somewhat to the right side with respect to the rotary knob 22. Due to the bayonet design of the grooves 25, the pins 33, after their straight insertion into the grooves 25, can be shifted together with the accumulator module 31 within the grooves 25 towards the left side in FIG. 2 up to the end 18. In this position the pins 33 are then retained against being pulled off by the walls of the grooves 25 located in the drawing plane of FIG. 2. At the same time, during this shifting towards the left side in FIG. 2, the spring 26 at the outer wall 27 of the housing 21 snaps into the recess 34 of the accumulator module 31 due to its bias towards this direction, whereby the engagement between the accumulator module 31 and the housing 21, and thus the head band, is effected. Detaching the accumulator module 31 from the housing 21 is done vice versa by shifting the accumulator module 31 in FIG. 2 towards the right side, whereby the snap engagement between the spring 26 and the recess 34 is cancelled and the pins 33 can be pulled out of the free areas of the grooves 25.

LIST OF REFERENCE NUMERALS 11 front support part
12 back support part
13 upper support part
14/15 ends of the head band
18 end of the groove
21 flat housing
22 rotary knob
23/24 rim of the housing
25 groove
26 spring
27 outer wall
28 inner wall
29 lining
31 accumulator module
32 opening
33 pins
34 recess
35 three-pole plug sockets
37 upper longitudinal edge
38 lower longitudinal edge
40 diagnostic instrument
42 light source

What is claimed is:

1. A headband for diagnostic instruments, said headband comprising:

a closed front support part;

an open back support part having two opposite ends;

a mechanism for adjusting and fixing the length of said headband and associated to said ends of said open back support part, said mechanism being arranged in a housing substantially adapted to a shape of a human head and having a shank extending through a wall of said housing and comprising a rotary knob; and an accumulator module detachably mounted at said housing and having an opening for a passage of said shank and said rotary knob;

wherein said housing is a flat housing having two opposing rims, wherein two spaced-apart bayonet-type grooves are formed in each of said opposing rims of said flat housing and wherein said flat housing has a resilient spring protruding from an outer wall thereof;

said opening in said accumulator module is a central, fully bordered opening having a shape which is adapted to the geometry of said rotary knob for operation thereof;

said accumulator module has pins arranged for engagement within said grooves in said flat housing and for lateral shifting within said grooves such that said pins occupy a fixed position in said grooves; and said accumulator module has a recess for snap engagement with said resilient spring of said flat housing in a fixed position of said pins in said grooves.

2. The headband in accordance with claim 1, wherein said pins are arranged at equal lateral distances to said opening.

3. The headband in accordance with claim 1, wherein thicknesses of each of said outer wall and an inner wall of said flat housing substantially correspond to a thickness of said headband.

4. The headband in accordance with claim 1, wherein said accumulator module comprises narrow end sides, in the area of each of said narrow end sides a three-pole plug socket for a cable connection being provided.

5. The headband in accordance with claim 1, wherein said accumulator module, on a side thereof facing away from said flat housing, is tapered towards said opening.

6. The headband in accordance with claim 1, wherein said closed front support part is configured to hold a diagnostic instrument having a light source.

7. The headband in accordance with claim 6, wherein said accumulator module includes an electrical facility for connection to said light source.

* * * * *